(12) United States Patent
Wang et al.

(10) Patent No.: US 8,192,660 B2
(45) Date of Patent: Jun. 5, 2012

(54) COLD-WATER SOLUBLE EXTRUDED STARCH PRODUCT

(75) Inventors: Lin Wang, Iowa City, IA (US); Pete Miller, Davenport, IA (US); Jeff Underwood, Muscatine, IA (US); Tonya Armstrong, Muscatine, IA (US); Michael Kramer, Muscatine, IA (US); Susan Freers, Muscatine, IA (US); Roger McPherson, Muscatine, IA (US); E. Daniel Hubbard, West Liberty, IA (US); Terry Andren, Grover, MO (US)

(73) Assignee: Grain Processing Corporation, Muscatine, IA (US)

( * ) Notice: Subject to any disclaimer, the term of this patent is extended or adjusted under 35 U.S.C. 154(b) by 3294 days.

(21) Appl. No.: 10/687,471

(22) Filed: Oct. 15, 2003

(65) Prior Publication Data
US 2005/0260316 A1 Nov. 24, 2005

Related U.S. Application Data

(62) Division of application No. 09/863,928, filed on May 23, 2001, now Pat. No. 7,595,015.

(60) Provisional application No. 60/207,019, filed on May 25, 2000.

(51) Int. Cl.
*B29C 47/00* (2006.01)
*B29C 9/06* (2006.01)

(52) U.S. Cl. ............. 264/141; 264/165; 264/211.11

(58) Field of Classification Search ............. None
See application file for complete search history.

(56) References Cited

U.S. PATENT DOCUMENTS

| 3,427,951 | A | | 2/1969 | Mitan et al. |
|---|---|---|---|---|
| 3,904,429 | A | | 9/1975 | Eastman et al. |
| 4,076,846 | A | * | 2/1978 | Nakatsuka et al. ............. 426/62 |
| 4,623,549 | A | | 11/1986 | Katt et al. |
| 5,000,783 | A | * | 3/1991 | Dingeman et al. ............. 75/321 |

(Continued)

FOREIGN PATENT DOCUMENTS

CA 1 040 920 10/1978

(Continued)

OTHER PUBLICATIONS

Curic et al. Enzymatic Conversion of Corn Starch in Twin-Screw Extruder, Chem Biochem, Eng. Q. University of Zagreb, Zagreb, Croatia, 12 (2), 63-71 (1998).

(Continued)

*Primary Examiner* — Monica A Huson
(74) *Attorney, Agent, or Firm* — Fitch, Even, Tabin & Flannery, LLP (57) ABSTRACT

Disclosed is a cold-water soluble starch and a process for preparing same. Generally, the process comprises providing a hydroxyalkyl starch and applying a shearing force to the starch in an extruder in the presence of moisture, the force and the moisture each being sufficient to gelatinize at least substantially all of the granules of the starch to thereby form a sheared starch. The starch is heated to its gelatinization temperature after the starch has passed partially through the barrel of the extruder, with the moisture being maintained at a level sufficiently high to allow gelatinization but sufficiency low to protect the starch from becoming too sticky to extrude. The extruded starch product thus formed may be used in connection with a number of film-forming, coating, and other applications.

7 Claims, 5 Drawing Sheets

U.S. PATENT DOCUMENTS

| | | | |
|---|---|---|---|
| 5,455,342 A | * | 10/1995 | Redding, Jr. .................. 536/102 |
| 5,849,233 A | | 12/1998 | Altieri et al. |
| 6,001,408 A | | 12/1999 | Dudacek et al. |
| 6,200,623 B1 | | 3/2001 | Dudacek et al. |
| 6,218,321 B1 | | 4/2001 | Lorcks et al. |
| 6,247,394 B1 | | 6/2001 | Huber et al. |

FOREIGN PATENT DOCUMENTS

| | | |
|---|---|---|
| CA | 1 286 533 | 7/1991 |
| EP | 0 313 298 | 4/1989 |
| EP | 0374993 | 6/1990 |
| EP | 0 781 807 | 7/1997 |
| FR | 1175962 | 4/1959 |
| GB | 1 466 019 | 3/1977 |
| JP | 51 138772 | 11/1976 |
| JP | 55 96064 | 7/1980 |
| JP | 01 287101 | 11/1989 |
| JP | 03 0191729 | 8/1991 |
| JP | 07 023761 | 1/1995 |
| WO | WO 00/08945 | 2/2000 |
| WO | WO 00/75192 | 12/2000 |
| WO | WO 02/074814 | 9/2002 |

OTHER PUBLICATIONS

Fetzer et al., "The Estimation of Starch Paste Fluidities." Cereal Chemistry, American Association of Cereal Chemists, U.S.A., 36 (2), 108-127 (1959).

Suknark et al., "Physical properties of Directly Expanded Extrudates Formulated from Partially Defatted Peanut Flour and Different Types of Starch." Food Research International, 30 (8), 575-583 (1997).

* cited by examiner

Fig. 1. DSC Thermograms of the starch described.

COLD-WATER SOLUBLE EXTRUDED STARCH PRODUCT

RELATED APPLICATIONS

This divisional application claims priority to prior U.S. non-provisional application Ser. No. 09/863,928, filed 23 May 2001, now U.S. Pat. No. 7,595,015, the entire contents of which are hereby incorporated by reference, which claimed priority to prior U.S. Provisional App 60/207,019, filed 25 May 2000, the entire contents of which are herby incorporated by reference.

TECHNICAL FIELD OF THE INVENTION

The invention is in the field of starches and starch derivatives. More particularly, the invention relates to a cold-water soluble extruded hydroxyalkyl starch product, and to films, coatings, and other products composed therefrom.

BACKGROUND OF THE INVENTION

Food, pharmaceutical, and industrial films and coatings contain a polymeric base that often is supplemented with plasticizers, detacifiers, surfactants, and coloring agents. Typically used polymers include gums; cellulose derivatives or hydrolysis products; synthetic polymers such as polyvinyl alcohol, polyvinyl acetate, polyurethane, polystyrene or polyvinylpyrrolidone; gelatin; dextrins; modified cook-up-starches, and combinations of the foregoing. These polymers are often very expensive or difficult to use, or have reduced acceptance by certain segments of the consuming public. In recent years, greater emphasis has been placed on replacing all or part of these polymer systems with more economical consumer-friendly starch-based polymers.

Many starch materials have been used to make a variety of films, foams, and other industrial and food products. However, despite the variety of starch materials available, known starches generally can be somewhat unsuitable for use in these applications. For instance, native starches have two key limitations when used in films and coatings. Films made from unmodified or "reduced viscosity" starches generally are brittle, weak, cloudy, and opaque, and cooking is generally required to hydrate the starch polymers, inasmuch as native starches typically are water insoluble at temperatures at or below room temperature (25° C.). The problems of brittleness, clouding and opacity can be mitigated somewhat with a low degree of hydroxyalkylation of amylose and/or amylopectin contained in the starch to form a hydroxyalkyl starch, but still the hydroxyalkyl starch will be cold-water insoluble. Thus, such starches are not useful where heating is not available.

To overcome the problem of cold-water insolubility, the starch may be physically or chemically modified, or may be enzymatically treated. One approach known in the art is to modify the starch by using alkylene oxide reagents, such as propylene, oxide, ethylene oxide, and the like. This process generally requires the use of organic solvents, such as ethanol, which are undesired due to the additional processing costs associated with such solvents.

The prior art also has taught to hydroxyalkylate the starch using an aqueous process. The hydroxyalkyl starch thus prepared is then cooked by drum-drying or spray-drying, and is ground to be marketed as a pre-gelled or "instant" starch. While such pre-gelled starches are suitable for some applications, such starches are difficult to disperse in water in low temperatures. Starches used in film and coating applications may contain intact starch granules, which can result in poor film clarity and increased film opacity. Particularly in the case of drum-dried starches, large lumps, sometimes referred to as "fish-eyes," are often formed. Also, the viscosity of these starches often is high, thus limiting the level of solids, which can be dispersed in an aqueous system without resulting in mixing and handling problems. Moreover, while occasionally additives such as borax, boric acid, gum arabic, and sulfate salts are added to improve wettability or dispersability, these solutions are somewhat unsatisfactory because of the additional costs required for such additional ingredients.

Attempts also have been made to formulate a pre-gelled, starch using an extruder. However, such attempts often have resulted in processing difficulties, particularly when modified starches are extruded under conditions of low moisture. For example, U.S. Pat. No. 5,849,233 discloses a method of extruding starch. This reference recognizes processing difficulties in extruding starches, and purports to teach that these difficulties can be overcome by employing as a feed starch a starch with a coarse particle size. However, the process requires additional drying and conditioning equipment, and can entail extra processing costs. Other efforts to extrude starch (e.g., as shown in International Publication WO 00/08945, U.S. Pat. No. 3,904,429 and Canadian patent, 1,286,533) have not provided a cold water soluble starch that is film-forming in aqueous solution. The invention seeks to address these shortcomings in the art.

SUMMARY OF THE INVENTION

Surprisingly, it has been found that hydroxyalkyl starches can satisfactorily be extruded without encountering the difficulties found in prior art processes or requiring the unusually coarse particle size required of the prior art. The extruded hydroxyalkyl starches prepared in accordance with the invention are cold-water soluble and film-forming in aqueous solution, and are useful in a number of applications.

In accordance with the invention, a process for preparing a cold-water soluble starch is provided. The process comprises providing a hydroxyalkyl starch, generally in granular form, and applying a shearing force to the starch in the presence of moisture in an extruder. The conditions in the extruder are controlled in a manner not heretofore known to provide a starch product that surprisingly is soluble in water at 25° C. and that is film-forming in aqueous solution. Generally, an extruder having a barrel, a die, and at least one rotating shaft is provided. The barrel includes at least first and second zones, the first zone being upstream from the second zone. The zones are typically defined by plural heads in the extruder barrel. In extruding the starch, the total moisture in the extruder is kept below about 25%. The temperature in the first zone is maintained at a level insufficient to gelatinize the starch at the moisture content in the barrel, and the temperature in the second zone is maintained at a level that is sufficient to gelatinize the starch. Additionally, the rotational speed of the shaft is controlled to impart a specific mechanical energy to the starch that is sufficient to result in a soluble extruded starch product that is capable of extrusion through the die, i.e., that is not overly tacky or otherwise not susceptible to extrusion. The extruded starch then may be cut, dried, and ground. The cold-water soluble starch thus prepared will be particularly suitable for use in connection with films, coatings, and like applications. Moreover, the invention is applicable to hydroxyalkyl starches having a conventional particle size distribution, and there is no need to use feed starch having an unusually coarse particle size.

DESCRIPTION OF THE PREFERRED EMBODIMENT

The starting feed starch used in connection with the invention is a hydroxyalkyl starch, which may be derived from any suitable plant source, such as corn, potato, wheat, rice, sago, tapioca, high amylose corn, waxy maize, sorghum, and so forth. The hydroxyalkyl starch may be obtained commercially, or a native starch may be hydroxylated in accordance with known methods, such as those described in *Starch: Chemistry and Technology*, Whistler, et al., ed. (1984), pp. 343-49. The hydroxyalkyl starch may be otherwise modified, before, after or during hydroxyalkylation, such as via acid hydrolysis, enzyme treatment, heat treatment, oxidation, cross-linking or the like. Preferably, the feed starch is an acid-thinned hydroxypropyl corn starch. Most preferably, the starch has a particle size distribution such that at least 90% by weight of the starch granules pass through an 80-mesh (180 micron) screen. Such starch is cold-water insoluble, and must be cooked to form a paste. The hydroxyalkyl starch should be derivatized with a substituent having from 2 to 6 carbon atoms, and the degree of substitution (DS) of the starch may be any value suitable to provide a film-forming starch.

Figure 8:
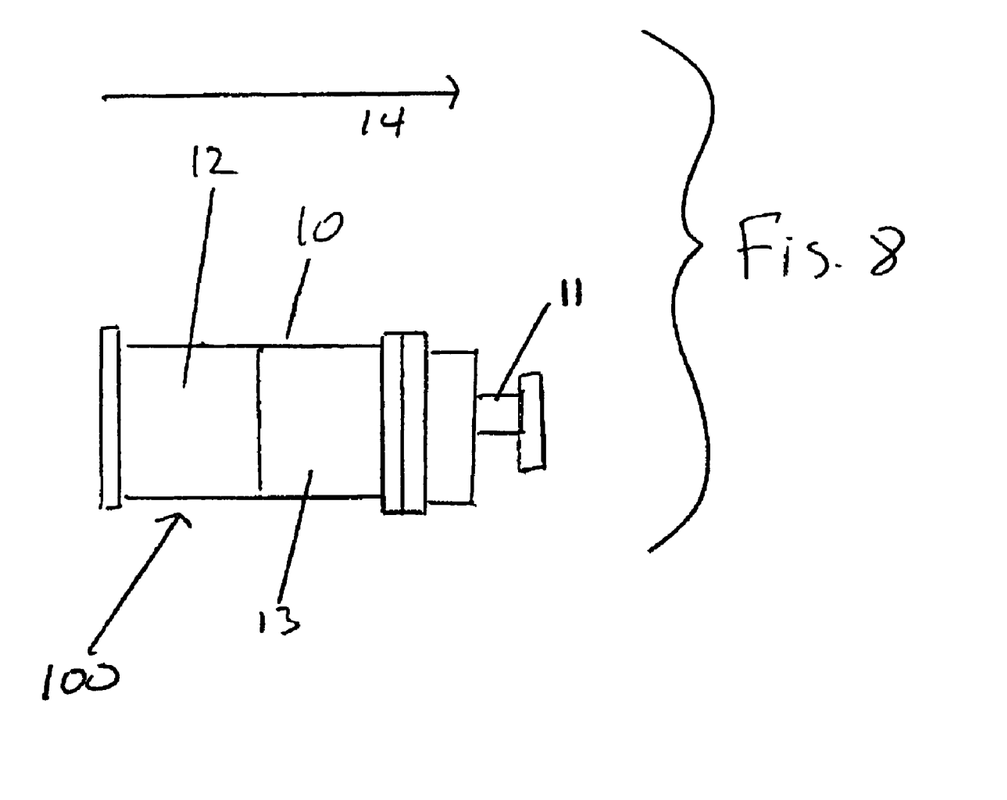
FIG. 8 is a representational view illustrating an extruder useful in conjunction with the invention.

In accordance with the invention, the feed starch is subjected to a shearing force, moisture and heat sufficient to gelatinize all or substantially all of the granules of the feed starch. The shearing force is applied by introducing the feed starch into an extruder, which, in accordance with the invention, may be a single screw extruder or a twin screw extruder or other suitable extruder. As shown in FIG. 8, the extruder 100 generally includes a barrel 10 and a die 11 (in practice the extruder may include many other components, such as preconditioners, steam or water jackets, and numerous other components as may be conventional or otherwise suitable for use in conjunction with the invention). The extruder barrel includes at least first and second zones 12, 13, which generally are defined by heads in the extruder. The direction of travel is illustrated by the arrow 14 in FIG. 8. Commercially available extruders useful in conjunction with the invention include those available from Wenger, such as the Wenger TX57 and TX144 extruders. The moisture content in the extruder barrel should be sufficient to gelatinize the starch, taking into account the moisture present in the feed starch (typically 9% to 12% by starch weight). Preferably, the moisture content is less than about 25% by weight (based on the total weight of dry starch and water in the barrel); more preferably, the moisture content is below about 22.5%; even more preferably, the moisture content is below about 20%; and even more preferably, the moisture content is below about 17.5%. The moisture may be added in the extruder preconditioner via addition of steam or liquid water. The preconditioner cylinder may be equipped with an agitator, such as a single agitator, dual agitators, or dual agitators with different speeds.

In operating the extruder, the temperature of the heads is such that the temperature in the first zone is not sufficient to gelatinize the starch, but the temperature in the second zone is sufficient to gelatinize the starch. The head temperature typically ranges from about 25° C. to 200° C. (it should be noted that the head temperature may be different from the actual temperature of the starch in the zone of the extruder). The extruder may have more than two zones; the invention may be performed in any such extruder so long as two zones meet the relationship heretofore described. More preferably, the temperature increases steadily in the extruder to thereby gradually cook the starch.

The invention also contemplates controlling the shaft speed of the extruder. The shaft speed typically ranges from 125 to 450 rpm, thus resulting in a retention time of from about 25 to 250 seconds. More generally, the shaft speed must be such as to provide a sufficient mechanical energy input that is sufficient to result in a starch product that is soluble in water at 25° C. If the specific mechanical energy input is too low, then the starch will be insufficiently hydrolyzed, leading to a starch that is not soluble. If the specific mechanical energy input is too high, the starch may become overly tacky, thus leading to problems with extrusion. Typically, the specific mechanical energy input will range from about 60 to about 150 kW/ton, although this and the other foregoing parameters may vary depending upon the extruder type.

Figure 2:
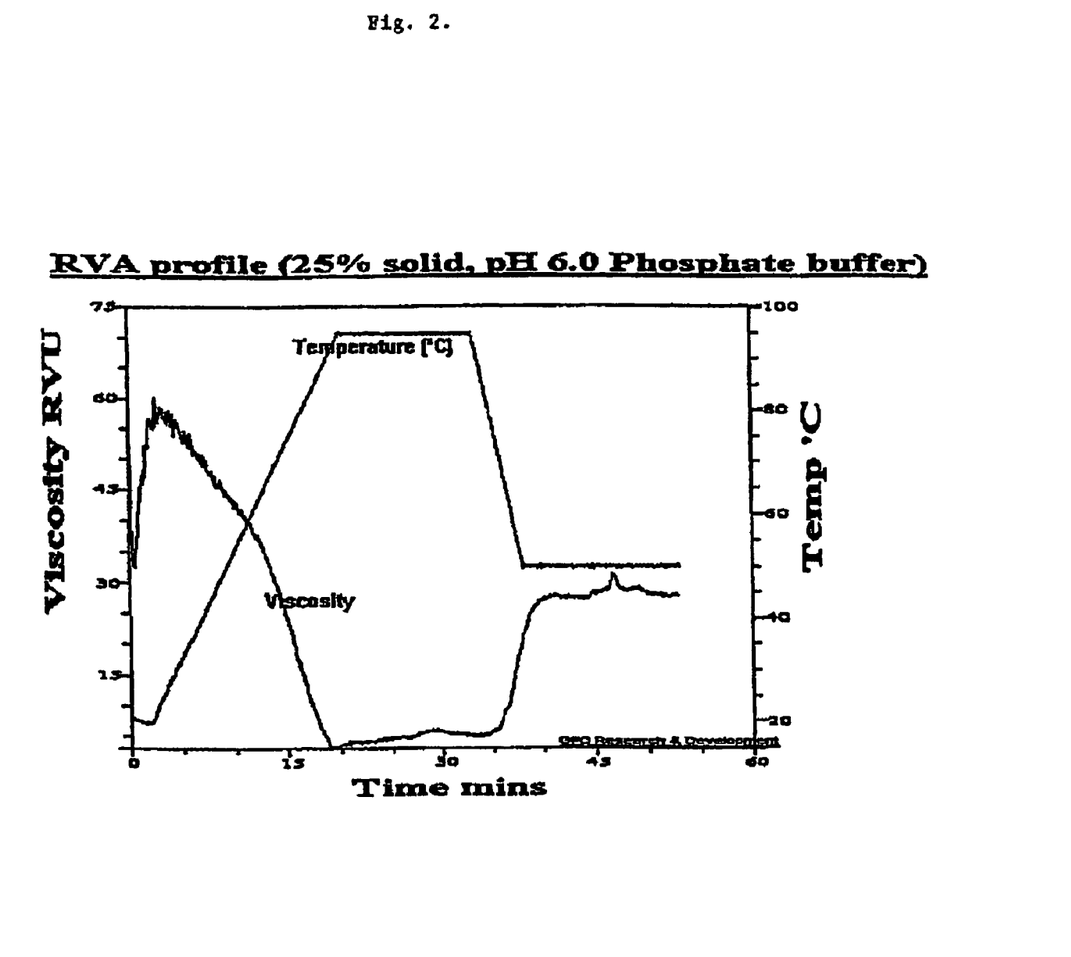
FIG. 2 is a rapid viscoanalyzer profile for a cold-water soluble starch prepared in accordance with the invention.

The extruded starch product thus formed will be an extruded mass, often an extruded starch product, that may be cut, dried, and ground to have any desired particle size distribution. An optimum particle size range is between 40 to 140 mesh (100-400 microns), with fewer than 30% of the particles passing through a U.S. 200-mesh (75 microns) screen. When a product is made with such particle size distribution, the product will exhibit good wettability. The product may have a viscosity range, as measured by a Brookfield Viscometer, from 100 to 300 cp at 15% solids at room temperature. A typical RVA (Rapid Visco Analyzer) profile is shown in FIG. 2.

Figure 1:
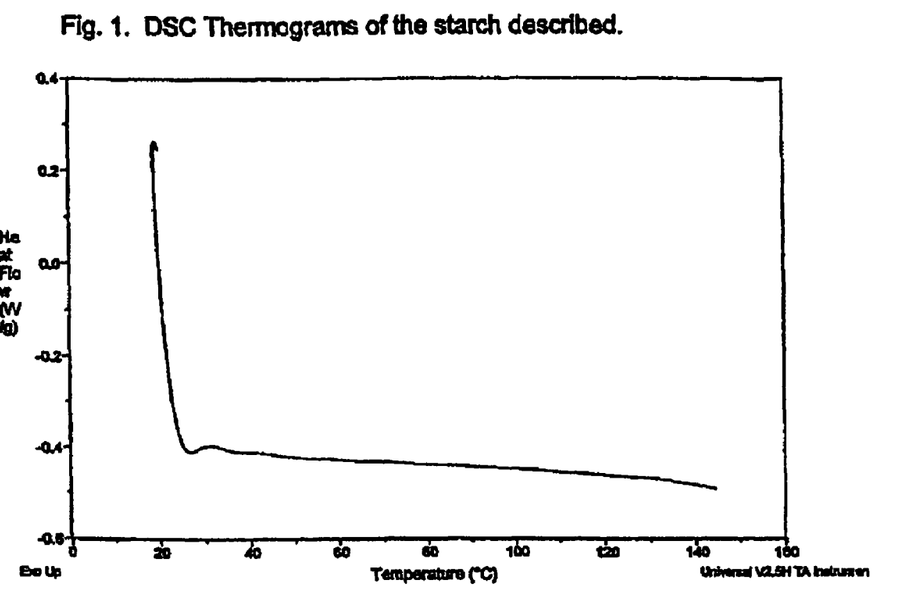
FIG. 1 is a differential scanning calorimetry thermogram of a cold-water soluble starch prepared in accordance with the invention.

The extruded starch product will be substantially free of starch granules, by which it is contemplated that the starch will be at least 95% gelatinized; this may be determined by an inspection of birefringence under a microscope using polarized light. FIG. 1 illustrates a differential scanning calorimetry thermogram at 10° C./min. from 20° to 140° C. of a mixture of one embodiment of the starch product of the invention and excess water (starch:water=1:3). No endothermic peaks normally expected for starch gelatinization are exhibited, thus signifying that the starch product is already gelatinized.

The starch product prepared in accordance with the invention also will be substantially completely cold-water soluble, i.e., soluble in water at 25° C. A method for determining solubility is described below. Other methods can be found in such publications as "Physical Properties of Extruded Wheat, Starch-Additive Mixtures," Singh et al., *Cereal Chemistry* 75 (3):325-30 (1998). In accordance with a preferred method for determining cold-water solubility, 9.0 g (dry basis) product is dispersed in 291.0 g of distilled water. After stirring for 30 minutes at room temperature, two 50 ml aliquots of the mixture are transferred into two centrifuge tubes and centrifuged at 2,000 rpm in a suitable centrifuge, such as an IEC CL2 laptop centrifuge, for 10 minutes. Twenty ml of each supernatant are then transferred to pre-weighed PYREX evaporating dishes, and the dishes are then weighed. The dishes are then placed on a steam bath to be evaporated to dryness. Residues are then dried in an oven at 105° C. for at least two hours, and the dried samples with dishes are then cooled to room temperature in a desiccator for at least two hours. The dishes are then weighed and recorded as a dry sample weight. Solubility is calculated using the following formula:

$$\text{Solubility} = [(\text{dry sample weight} - \text{tare}) \times 30000] / (9.00 \times \text{supernatant weight})$$

The product will be deemed cold-water soluble if the solubility is greater than 90%. A starch product prepared by the process of the invention may have a solubility greater than 99.0% by the method described.

The product prepared in accordance with the invention has an excellent film-forming property, and is particularly useful in connection with coatings. Films and coatings made of the product are clear, transparent, flexible, and strong at room temperatures. While it is not intended to limit the invention to a particular theory of operation, it is believed that the disruption of the starch granules leaves few granules intact to defract and defuse light, and to thereby cause opaqueness. The high shear encountered in the extruder also may realign the starch polymers in directions favorable to film-forming.

The starch product of the invention may be used in any application where a film, coating, barrier, or binding material is desired. The product also may be used in any application where filler, viscosity, solid, adhesive, or texture modification is needed, for example, in polishing/clear coat applications, oil/lipid barrier, adhesive, water or moisture or vapor barrier, oxygen barrier, or physical barrier, protective coating, encapsulation, fluidized bed purification, texture modification, flavor entrapment and preservation, flavor migration inhibition (especially from alcohol-based solvents), opaque maskings and coatings, imaging-forming films for printing, for example, edible inks, flavored coatings, colored coatings, free-standing films, tablet coatings, capsules, thickeners, materials for agglomeration, and the like. The product may be used in connection with food products, such as nut meats, ready-to-eat cereals, snack foods of many types, confections including soft-pan items, chocolate, marshmallows, pressed mints, chocolate pan pieces, and rolled pieces, molded chocolate bars, coffee beans, processed and unprocessed meats, and the like. The starch product also may be used in connection with industrial and consumer products, such as paper, corrugating board, cardboard boxes, detergents, cleaners, and the like, and in pharmaceutical applications such as tablets, tablet coatings, capsules, agglomeration ingredients, and so forth.

The product may be used in connection with other ingredients, including surfactants, polymers, fillers, and other ingredients as may be desired in a given application. As surfactants it is contemplated that those such as mono- and di-glycerides, di-acetyl tartaric esters of fatty acids, propylene glycol mono- and di-esters of fatty acids, polysorbate 60, calcium or sodium stearoyl 2 lactylate, lactyl stearate, sodium stearoyl fumarate, succinylate mono-glycerides, ethoxylated mono- and di-glycerides, and the like may be used. In certain applications, the starch may be used in conjunction with other natural polymers such as gums, cellulose derivatives, starch derivatives, starch hydrolysis products, microorganism products, or with synthetic polymers, such as polyvinyl alcohol, polyvinylacetate, polyurethane, polystyrene, polyvinyl pyrrolidone, and the like.

The product of the invention is particularly useful in connection with film-forming applications. In accordance with the invention, a film may be made by providing the starch of the invention, mixing the starch with sufficient water to solubilize the starch and, optionally but preferably including a plasticizer, such as glycerin, a polyethylene glycol, a propylene glycol, oleic acid, triacetin, or the like. The film thus prepared without any additive may have a tensile strength generally above 35 Mpa at 55-60% relative humidity and room temperature (as measured, for example, by an INSTRON apparatus equipped with a one-inch rubber-based grip).

The product also may be used in connection with an instant tack coating formulation. Such formulation preferably comprises water in an amount ranging from about 25% to about 85% by weight; the starch in an amount ranging from about 10% to about 25% by weight, and optionally a surface gloss agent; the surface gloss agent may serve to some extent as a plasticizer. Suitable surface gloss agents include, for example, maltodextrins, such as MALTRIN® M180 sold by Grain Processing Corporation of Muscatine, Iowa. When used, the surface gloss agent preferably is used in an amount ranging from about 5% to 50% by weight. More generally, any amount of water suitable to hydrate the starch and any amount of surface gloss agent suitable to impart surface gloss may be employed with or without colorants, flavoring agents, additional plasticizers, and the like.

The invention also encompasses a protective coating formulation, which generally comprises water, starch and a plasticizer and/or surfactant. Suitable plasticizers include glycerol and propylene glycol; one suitable surfactant is Polysorbate 80. These ingredients may be added in amounts suitable for their intended function.

The following Examples are provided to illustrate the present invention, but should not be construed as limiting the invention in scope.

EXAMPLE 1

Cold Water Soluble Acid-Thinned Hydroxypropyl Starch

Figure 3:
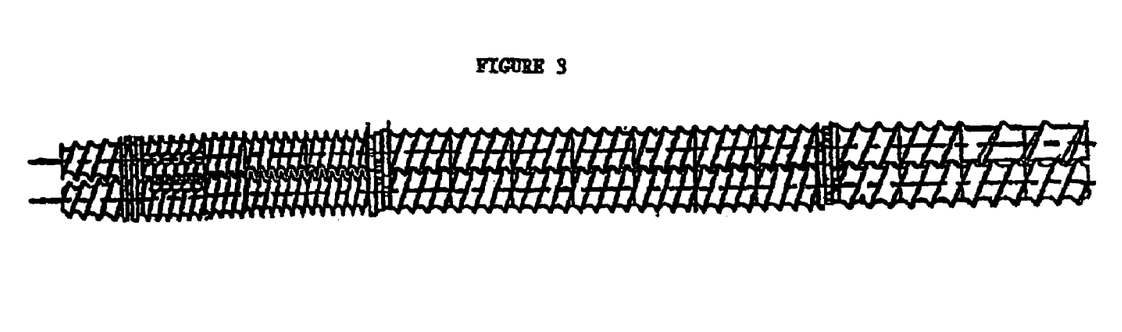
FIG. 3 is a side view illustrating the screw configuration shown for the extruder used in Example 1.

An acid-thinned hydroxypropyl starch (B790 PURE-COTE® starch, available from Grain Processing Corporation, Muscatine, Iowa) having a moisture content of about 11% and having a particle size such that more than 90% by weight of the starch passed through a US 80-mesh screen was extruded on a Wenger TX144 Twin Screw Extruder according to the following conditions to give an expanded product. The expanded product was dried in a fluid bed dryer. The screw configuration of the extruder was as shown in FIG. 3 and was set such that the starch was cooked and sheared to an extent such that no significant amount of intact granules remained. The extrusion conditions were as follows.

|  | 1A | 1B | 1C | 1D | 1E | 1F | 1G |
|---|---|---|---|---|---|---|---|
| Raw Material Information | | | | | | | |
| Substrate | B790 | B790 | B790 | B790 | B790 | B790 | B790 |
| Dry Recipe % moisture | 11.6 | 11.6 | 11.6 | 11.6 | 11.3 | 11.3 | 11.3 |
| Feed Starch Rate (lb/hr) | 4200 | 4275 | 4300 | 4400 | 4400 | 4500 | 4500 |
| Cylinder Information | | | | | | | |
| Steam Flow to Cylinder lb/hr | 84 | 85 | 85 | 86 | 86 | 97 | 91 |
| Water Flow to Cylinder lb/hr | 107 | 107 | 109 | 108 | 110 | 113 | 115 |
| Extrusion Information | | | | | | | |
| Extruder Shaft Speed rpm | 360 | 360 | 360 | 360 | 360 | 360 | 360 |
| Extruder Motor Load % | 79 | 80 | 78 | 84 | 80 | 79 | 78 |
| Steam Flow to Extruder lb/hr | 0 | 0 | 0 | 0 | 0 | 0 | 0 |
| Water Flow to Extruder lb/hr | 105 | 106 | 109 | 109 | 111 | 115 | 113 |
| $1^{st}$ Head Temp | 101° F. | 144° F. | 95° F. | 127° F. | 95° F. | 110° F. | 97° F. |
| $2^{nd}$ Head Temp | 195° F. | 192° F. | 192° F. | 190° F. | 190° F. | 191° F. | 190° F. |
| $3^{rd}$ Head Temp | 225° F. | 225° F. | 225° F. | 225° F. | 225° F. | 225° F. | 225° F. |
| $4^{th}$ Head Temp | 258° F. | 266° F. | 274° F. | 273° F. | 269° F. | 264° F. | 265° F. |
| $5^{th}$ Head Temp | 320° F. | 287° F. | 312° F. | 313° F. | 319° F. | 372° F. | 306° F. |
| $6^{th}$ Head Temp | 280° F. | 240° F. | 200° F. | 160° F. | 170° F. | 255° F. | 265° F. |
| Specific Mechanical Energy kW/ton | 100.0 | 106.2 | 103.4 | 100.7 | 102.0 | 99.3 | 98.2 |
| Product Assay | | | | | | | |
| Moisture (%) | 6.9 | 6.5 | 6.9 | 6.6 | 6.3 | 6.5 | — |
| Solubility (%) | 99.9 | 100 | 100 | 100 | 100 | 100 | 100 |

For each of these examples, the extruder specific mechanical energy inputs was greater than 80 kW/ton. The SME, shaft speed, temperature profile, and moisture content were used to monitor and control the extrusion process.

EXAMPLE 2
Cold Water Soluble Acid-Thinned Hydroxypropyl Starch

Figure 4:
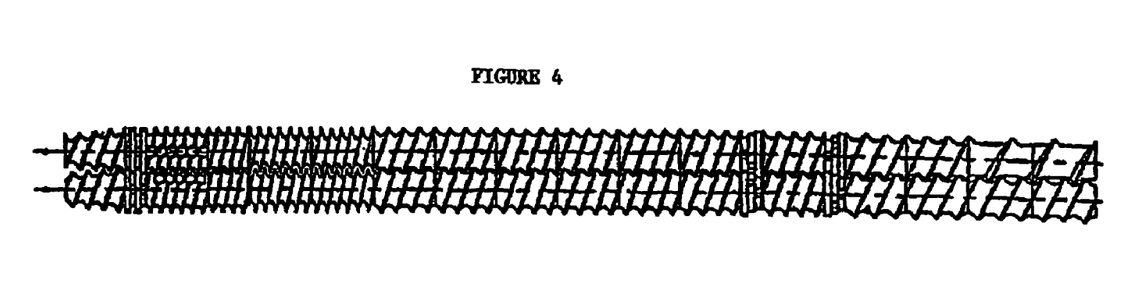
FIG. 4 is a side view illustrating the screw configuration shown for the extruder used in Example 2.

A hydroxypropyl starch (B760 PURE-COAT®, available from Grain Processing Corporation of Muscatine, Iowa) was extruded on a Wenger TX57 Twin Screw Extruder having the screw configuration shown in FIG. 4 and under the following conditions to yield an expanded product, which was dried in a moving grate dryer. The conditions were as follows.

|  | 2A | 2B | 2C | 2D | 2E | 2F | 2G |
|---|---|---|---|---|---|---|---|
| Raw Material Information | | | | | | | |
| Substrate | B760 | B760 | B760 | B760 | B760 | B760 | B760 |
| Dry Recipe % moisture | 10-11 | 10-11 | 10-11 | 10-11 | 10-11 | 10-11 | 10-11 |
| Feed Starch Rate (lbs/hr) | 350 | 350 | 250 | 270 | 290 | 310 | 330 |
| Cylinder Information | | | | | | | |
| Steam Flow to Cylinder lb/hr | 12 | 12 | 12 | 12 | 12 | 12 | 12 |
| Water Flow to Cylinder lb/hr | 8 | 8 | 8 | 8 | 8 | 8 | 8 |
| Extrusion Information | | | | | | | |
| Extruder Shaft Speed rpm | 350 | 350 | 250 | 270 | 290 | 310 | 330 |
| Extruder Motor Load % | 51 | 51 | 35 | 40 | 41 | 46 | 47 |
| Steam Flow to Extruder lb/hr | 0 | 0 | 0 | 0 | 0 | 0 | 0 |
| Water Flow to Extruder lb/hr | 10 | 10 | 10 | 10 | 10 | 10 | 10 |
| $1^{st}$ Head Temp | 98° F. | 97° F. | 96° F. | 96° F. | 95° F. | 95° F. | 97° F. |
| $2^{nd}$ Head Temp | 135° F. | 136° F. | 124° F. | 125° F. | 125° F. | 126° F. | 126° F. |
| $3^{rd}$ Head Temp | 144° F. | 198° F. | 129° F. | 131° F. | 132° F. | 135° F. | 136° F. |
| $4^{th}$ Head Temp | 179° F. | 180° F. | 176° F. | 175° F. | 175° F. | 180° F. | 180° F. |
| $5^{th}$ Head Temp | 292° F. | 295° F. | 231° F. | 233° F. | 233° F. | 236° F. | 239° F. |
| Specific Mechanical Energy kW/ton | 79 | 79 | 76 | 81 | 77 | 81 | 78 |

The starches produced were substantially completely soluble (over 99%).

EXAMPLE 3

Figure 5:
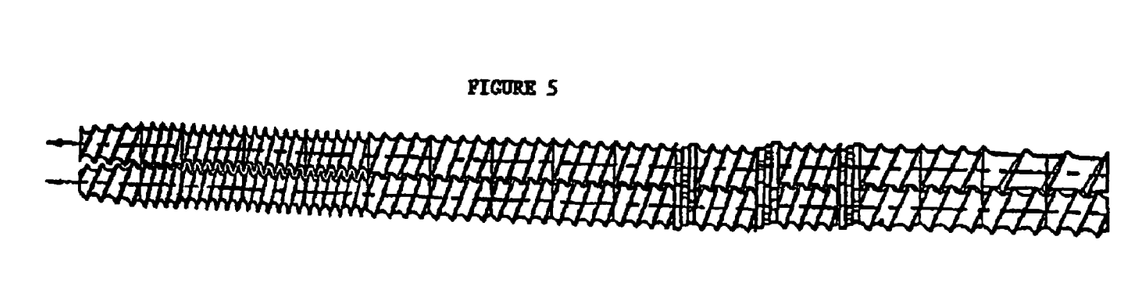
FIG. 5 is a side view illustrating the screw configuration shown for the extruder used in Example 3.

The starch used in Example 1 was extruded on a Wenger TX57 Twin Screw Extruder according to the following conditions and with the screw configuration shown in FIG. 5.

| Raw Material Information | |
|---|---|
| Substrate | B790 |
| Dry Recipe % moisture | ~11% |
| Dry Recipe Rate lb/hr | 175 |
| Feed Screw Speed rpm | 15 |
| Cylinder Information | |
| Cylinder Speed rpm | 278 |
| Steam Flow to Cylinder lb/hr | 0 |
| Water Flow to Cylinder lb/hr | 0 |
| Extrusion Information | |
| Extruder Shaft Speed rpm | 398 |
| Extruder Motor Load % | 42 |
| Steam Flow to Extruder lb/hr | 0 |
| Water Flow to Extruder lb/hr | 11 |
| Knife Speed rpm | 459 |
| No. of Knives | 2 |
| $1^{st}$ Head Temp | 77° F. |
| $2^{nd}$ Head Temp | 78° F. |
| $3^{rd}$ Head Temp | 108° F. |
| $4^{th}$ Head Temp | 133° F. |
| $5^{th}$ Head Temp | 270° F. |
| $6^{th}$ Head Temp | |
| Die Hole Size & How many? | 3 mm/15 |
| Die Pressure psi | 500 |
| Vacuum on/off inches of vac? | OFF |
| Specific Mechanical Energy kW/ton | 148 |

The expanded, friable product thus formed needed no drying. The product was ground on a Wiley Mill followed by an Alpine Mill to give a powder.

The powder was mixed into water at room temperature. A paste was formed, thus evidencing the gelatinized nature of the product. The paste was drawn into a thin film using a Meyer Road and then left to dry overnight at 50% relative humidity and 72° F. to form a clear, transparent film.

EXAMPLE 4

Cold Water Soluble Hydroxypropyl Starch

Figure 6:
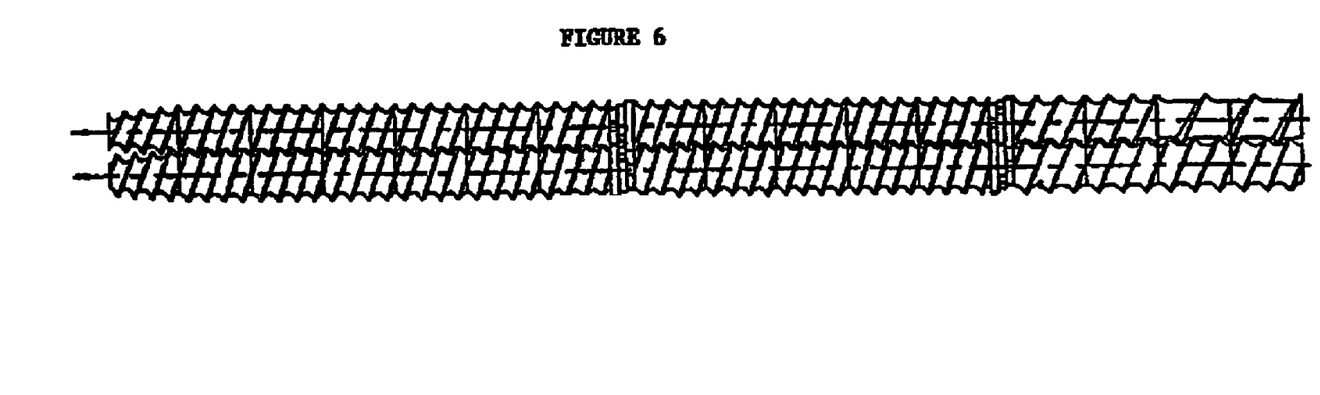
FIG. 6 is a side view illustrating the screw configuration shown for the extruder used in Example 4.

A cross-linked hydroxypropyl starch (B992 PURE-GEL®, available from Grain Processing Corporation of Muscatine, Iowa), and having a moisture content of about 11% was extruded on a Wenger TX52 Twin Screw Extruder according to the conditions provided below and using the screw configuration shown in FIG. 6.

| | 4A | 4B | 4C |
|---|---|---|---|
| Raw Material Information | | | |
| Substrate | B992 | B992 | B992 |
| Dry Recipe % moisture | ~11 | ~11 | ~11 |
| Feed Screw Rate rpm | 12 | 12 | 12 |
| Cylinder Information | | | |
| Cylinder Speed rpm | 110 | 110 | 110 |
| Steam Flow to Cylinder lb/hr | 0 | 0 | 0 |
| Water Flow to Cylinder lb/hr | 27.1 | 27.1 | 27.1 |
| Extrusion Information | | | |
| Extruder Shaft Speed rpm | 160 | 160 | 160 |
| Extruder Motor Load % | 29 | 28 | 17 |
| Steam Flow to Extruder lb/hr | 0 | 0 | 6.4 |
| Water Flow to Extruder lb/hr | 5.5 | 16.7 | 4.8 |
| $1^{st}$ Head Temp | | | |
| $2^{nd}$ Head Temp | 32° C. | 33° C. | 42° C. |
| $3^{rd}$ Head Temp | 32° C. | 33° C. | 42° C. |
| $4^{th}$ Head Temp | 90° C. | 90° C. | 90° C. |
| $5^{th}$ Head Temp | 90° C. | 90° C. | 90° C. |
| $6^{th}$ Head Temp | 65° C. | 65° C. | 65° C. |
| $7^{th}$ Head Temp | 62° C. | 57° C. | 65° C. |
| $8^{th}$ Head Temp | 62° C. | 57° C. | 65° C. |
| $9^{th}$ Head Temp | 63° C. | 63° C. | 65° C. |
| Die Pressure kPa | 1720 | 70 | 2760 |

The extruded product, which was in the form of a condensed bead was dried on a moving grate dryer and then ground into a powder.

Each powder was mixed into water at room temperature to give pastes at 12% solids (thus evidencing the gelatinized nature of the extruded product). The pastes were evaluated for gel strength and clarity. Gel strength was determined using a Texture Analyzer, Stevens LFRA Texture Analyzer TA 1000, 1 cm diameter probe after one day refrigeration at 40° F. Clarity was determined by observation on a scale of 0 to 9, 0 being opaque and 9 being clearest. The following results were obtained.

| Evaluation Test | Water Temperature | 4A | 4B | 4C | B992 Starch (control) |
|---|---|---|---|---|---|
| Gel Strength | 30° C. | 26 | 25 | 26 | * |
| | 40° C. | 24 | 49 | 51 | * |
| | 50° C. | 50 | 56 | 60 | 48 |
| | 65° C. | 49 | 60 | 62 | 103 |
| Clarity | 30° C. | 1 | 1 | 1 | * |
| | 40° C. | 3 | 5 | 4 | * |
| | 50° C. | 7 | 7 | 6 | 0 |
| | 65° C. | 9 | 8 | 8 | 8 |

* The control, B992 Starch, was not amenable to testing at 30° C. and 40° C.

Starch B992 was not amenable to testing at 30° and 40° because these temperatures were too low to allow this starch to gelatinize. Gel strength reflects the thickening power of a product when the product is mixed with water (generally, a higher gel strength is preferred in many applications).

EXAMPLE 5

Cold Water Soluble Hydroxyethyl Starch

Figure 7:
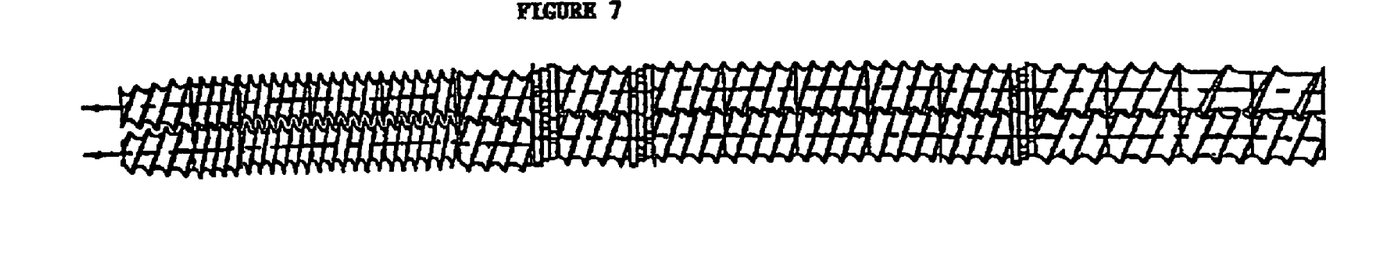
FIG. 7 is a side view illustrating the screw configuration shown for the extruder used in Example 5.

A hydroxyethyl starch (K95F COATMASTER® starch available from Grain Processing Corporation of Muscatine, Iowa) and having a moisture content of about 11% was extruded on a Wenger TX57 Twin Screw Extruder under the following conditions and having the screw configuration shown in FIG. 7.

| Raw Material Information | |
| --- | --- |
| Substrate | K95F |
| Dry Recipe % moisture | ~11% |
| Dry Recipe Rate lb/hr | 146 |
| Feed Screw Speed rpm | 8 |
| Cylinder Information | |
| Cylinder Speed rpm | 3498 |
| Steam Flow to Cylinder lb/hr | 0 |
| Water Flow to Cylinder lb/hr | 0 |
| Extrusion Information | |
| Extruder Shaft Speed rpm | 324 |
| Extruder Motor Load % | 32 |
| Steam Flow to Extruder lb/hr | 0 |
| Water Flow to Extruder lb/hr | 13 |
| Knife Speed rpm | 1087 |
| No. of Knives | 1 |
| $1^{st}$ Head Temp | 85° F. |
| $2^{nd}$ Head Temp | 169° F. |
| $3^{rd}$ Head Temp | 175° F. |
| $4^{th}$ Head Temp | 203° F. |
| $5^{th}$ Head Temp | 245° F. |
| $6^{th}$ Head Temp | |
| Die Hole Size & How many? | 3/36 |
| Die Pressure psi | 200 |
| Vacuum on/off inches of vac? | OFF |
| Specific Mechanical Energy kW/ton | 110 |

The product was made into an aqueous paste containing 35% extrudate at room temperature (thus evidencing the gelatinized nature of the product). The paste was tested in a Rapid Visco-Analyzer (Newport Scientific) by monitoring the rotational viscosity and was found to have a viscosity of 1800 cP at 50° C. compared to a baseline viscosity measurement of the raw starting material of about 100 cP, thus evidencing the gelatinized nature of the extruded product. Additionally, when the paste was tested in a Rapid Visco-Analyzer by monitoring the rotational viscosity during a controlled heating of the paste, the product exhibited no gelatinization peak. The starting material exhibited a crisp, characteristic peak at 70° C.

EXAMPLE 6

Tack Coating and Cooked Products

The expanded starch from Example 1, 18 parts by weight, was blended with MALTRIN® M180 (a maltodextrin available from Grain Processing Corporation of Muscatine, Iowa), 9 parts by weight to form a dry blend. Water, 73 parts by weight, was added to a kettle and stirred with a powered mixer so as to create a vortex. The dry blend was slowly added to the vortex, and the contents were mixed for an additional 10 to 30 minutes to form an instant tack coating.

The tack coating may be applied to a dry feed product substrate, such as a corn curl, pretzels, snack mix, or like item. The product may be applied by spraying or ladling at a level of from about 1% to about 15% weight gain, including moisture. Seasonings, including savory seasonings such as Cajun, barbeque, cheese, mustard, ranch, Creole, and the like, or sweet seasonings such as sugar and pareils, may be added, and may be applied in any suitable manner, such as by hand or using a seasoning applicator. The resulting coated product preferably is dried in an oven at a temperature ranging from 300° F. to 450° F. to a moisture content of from about 3% to 5%.

EXAMPLE 7

Oil-Based Instant Costing

Soybean oil, 50 parts by weight, was added to a vessel equipped with good agitation. The cold water soluble starch from Example 1, 7 parts by weight, was added to the stirred oil and mixing was continued in order to achieve a smooth mixture. Water, 42 parts by weight, and lecithin, 1 part by weight, were added as an emulsifier and mixing was continued for 10 to 15 minutes in order to achieve a smooth mixture.

The coated product may be applied to a food substrate as discussed in Example 6. Preferably, the coated product is dried in an oven at 300° F. to 350° F. with forced air to a moisture content of from 3% to 5% in the finished product.

EXAMPLE 8

Coated Peanut Products

A dusting mixture was prepared by dry-blending together the product of Example 1, 50 parts by weight, and MALTRIN® M100 (a maltodextrin available from Grain Processing Corporation, Muscatine, Iowa), 50 parts by weight. Blanched, unroasted medium runner peanuts were placed in a 16" ribbed candy pan rotating at 20 to 25 RPM. A 50% sucrose solution was poured into the pan in an amount effective to just wet the nuts to give about a 2% weight gain. The dusting mixture was then applied until the surfaces of the dusted nuts appeared dry, to thus give about a 5 to 6% weight gain. The dusted nuts were then tumbled an additional 2 to 3 minutes, during which time they wet back. An additional dusting with the dusting mixture was administered in order to achieve a dry appearance. The dry appearing, dusted nuts were then recoated with the sucrose solution, and the resulting rewetted nuts were dusted to dryness again with the dusting mixture. This alternating procedure of wetting with the sucrose solution followed by dusting to dryness with the dusting mixture was repeated until a final dry appearing dusted nut resulted having a 75 to 100% weight gain as compared to the starting peanuts. The coated nuts were roasted in an oven at 300° F. for 40 minutes with occasional stirring to assure uniformity of the roast. The roasted coated nuts were cooled to room temperature and placed back into the ribbed pan rotating at 20 to 25 rpm. Subsequently, the instant tack coating formulation from Example 6 was sprayed onto the roasted coated nuts to provide approximately 0.5% weight gain in a rotating pan in order to create a slight tackiness. McCormick Barbecue Seasoning F76161, 6% to 8% weight gain was added, and the coated nuts were tumbled until the seasoning was well distributed.

The resulting coated product was dried in an oven to a moisture level of from 3% to 5%.

EXAMPLE 9

Trail Mix Coating and Product

A mixture was prepared by dry-blending together sugar, 25 parts by weight, the product of Example 1, 15 parts by weight, MALTRIN QD® M500 (a maltodextrin available from Grain Processing Corporation, Muscatine, Iowa), 5 parts by weight, and lecithin, 0.2 parts by weight. Water, 54.8 parts by weight, was added to a kettle and stirred with a powered mixer so as to create a vortex. The dry blend was slowly added into the water at the top edge of the vortex, and the contexts were mixed for an additional 10 minutes to form an instant trail mix coating.

The resulting coating was sprayed onto a commercially purchased trail mix, by a spray gun system in a tumbler at a level of 5% to 15% weight gain. The resulting coated trail mix was dried in an oven at 150° F. to a moisture content of 10 to 12%.

EXAMPLE 10

Tablet Coating

A coating for a ⅜" round lactose/micro-crystalline cellulose placebo tablet was made. The coating had the following composition.

| Formulation | |
|---|---|
| Ingredients | Percentage by Weight |
| Product from Example 1 | 12.0% |
| Water | 88.0% |
| | 100.0 |

To prepare the coating, the starch was mixed into water with good agitation. A Vector HiCoater HC 100 coating pan with 2 spraying guns was used to apply the coating onto the tablets to result in a 2% weight gain on the tablet. The coating pan was set at the following conditions.

| | |
|---|---|
| Inlet temperature | 60-65° C. |
| Exhaust temperature | 38-42° C. |
| Pan speed | 8 RPM |
| Process air flow | 590 CFM |
| Spray air volume | 125 atomize/50 pattern PSI |
| Spray rate | 130-150 ml/min. |

A plasticizer, such as glycerin, polyethylene glycols (PEG), propylene glycol (PG), oleic acid, triacetin, and the like can be used to improve the physical and mechanical properties of starch. Surfactants such as di-glycerides, tartaric acid esters of fatty acids, propyleneglyco mono and diesters of fatty acids, polysorbate 60, calcium or sodium stearoyl-2-lactylate, lactylic stearate, sodium stearoyl fumarate, succinylated monoglyceride, ethoxylated mono and diglycerides, and the like optionally may be used to provide hydrophilicity. Likewise, polymers of gums, cellulose derivatives, starch derivatives or hydrolysis products, and microorganism products, synthetic polymers such as polyvinyl alcohol, polyvinyl acetate, polyurethane, polystyrene, and polyvinylpyrrolidone, and so forth can be used to improve the performance of the starch, for example, by increasing the flexibility and strength of the film-coating.

EXAMPLE 11

Film Coating

A coating for a ⅜" round lactose/micro-crystalline cellulose placebo was made. The coating had the following composition.

| Formulation | |
|---|---|
| Ingredients | Percentage by Weight |
| Product of Example 1 | 5.0% |
| Hydroxypropyl methyl cellulose | 5.0% |
| Propylene glycol | 1.0% |
| Polysorbate 80 | 0.5% |
| PURE-DENT ® B815 corn starch NF* | 0.5% |
| Titanium Dioxide | 2.0% |
| Color | 0.2% |
| Water | 85.8% |
| | 100.0 |

*Available from Grain Processing Corporation, Muscatine, Iowa.

To prepare the coating, the starch was mixed into water with good agitation. A Vector HiCoater HC 100 coating pan with 2 spraying guns was used to apply the starch to tablets to result in a 3% weight gain on the tablets. The coating pan was set at the following conditions:

| | |
|---|---|
| Inlet temperature | 65-70° C. |
| Exhaust temperature | 40-45° C. |
| Pan speed | 8 RPM |
| Process air flow | 575-595 CFM |
| Spray air volume | 125 atomize/50 pattern PSI |
| Spray rate | 170-180 ml/min. |

EXAMPLE 12

The properties of the starch extrusion may be characterized in part by an Extruder Solubilization Point Value (ESPV), which may be calculated as follows.

$$ESPV = \frac{1.71 \times 10^6 \times (M + M_{ws}) \times D^4}{(T_h - T_l)(M(Fws\ Cps + Fww\ Cpw) + M_{ws}\ Cpw)(Ffww^5 \times M \times Afg)}$$

wherein
M=mass flow rate of starch through extruder (kg/s)
Mws=flow rate of water through extruder (kg/s)
D=diameter of extruder barrel (m)
$T_h$=highest head temperature in barrel (° C.)
$T_l$=lowest head temperature in barrel (° C.)
Fws=weight fraction of starch in feed
Fww=weight fraction of water in feed
Ffww=weight fraction of water in the barrel
Afg=grams of starch from viscosity test*(g)
Cps=specific heat capacity of starch (J/kg)
Cpw=specific heat capacity of water (4186 J/kg)

*From the method disclosed in "The Estimation of Starch Paste Fluidities." W. R. Fetzer and L. C. Kirst, *J. Cereal Chem.*, American Ass'n of Cereal Chemists, Vol. 36, No. 2 (U.S., March, 1959).

Preferably, the ESPV is greater than or equal to 1.0. Following is a table of extrusion conditions and ESPVs for the extruded starch of Examples 1, 2 and 3.

| Inputs | Ex. 3 | Ex. 1A | Ex. 1B | Ex. 1C | Ex. 1D | Ex. 1E | Ex. 1F | Ex. 1G |
|---|---|---|---|---|---|---|---|---|
| SME, kW/ton | 148 | 100 | 106.2 | 103.4 | 100.7 | 102 | 99.3 | 98.2 |
| M, lb/hr | 175 | 4200 | 4275 | 4300 | 4400 | 4400 | 4500 | 4500 |
| Mws, lb/hr | 11 | 296 | 298 | 303 | 303 | 307 | 325 | 319 |
| $T_h$, deg F. | 270 | 320 | 287 | 312 | 313 | 319 | 372 | 306 |
| $T_l$, deg F. | 77 | 101 | 144 | 95 | 127 | 95 | 110 | 97 |
| Fws | 0.89 | 0.884 | 0.884 | 0.884 | 0.884 | 0.887 | 0.887 | 0.887 |
| Fww | 0.11 | 0.116 | 0.116 | 0.116 | 0.116 | 0.113 | 0.113 | 0.113 |
| Ffww | 0.163 | 0.174 | 0.174 | 0.174 | 0.173 | 0.171 | 0.173 | 0.172 |
| Dia, mm | 57 | 144 | 144 | 144 | 144 | 144 | 144 | 144 |
| Afg | 36 | 36 | 36 | 36 | 36 | 36 | 36 | 36 |
| M/SME | 1.18 | 42.00 | 40.25 | 41.59 | 43.69 | 43.14 | 45.32 | 45.62 |
| ESPV | 1.0 | 1.1 | 1.7 | 1.1 | 1.3 | 1.1 | 0.9 | 1.2 |

| Inputs | Ex. 2A | Ex. 2B | Ex. 2C | Ex. 2D | Ex. 2E | Ex. 2F | Ex. 2G |
|---|---|---|---|---|---|---|---|
| SME, kW/lb | 79 | 79 | 76 | 81 | 77 | 81 | 78 |
| M, lbs/hr | 350 | 350 | 250 | 270 | 290 | 310 | 330 |
| Mws, lbs/hr | 30 | 30 | 30 | 30 | 30 | 30 | 30 |
| $T_h$, deg F. | 292 | 295 | 231 | 233 | 233 | 236 | 239 |
| $T_l$, deg F. | 98 | 97 | 96 | 96 | 95 | 95 | 97 |
| Fws | 0.895 | 0.895 | 0.895 | 0.895 | 0.895 | 0.895 | 0.895 |
| Fww | 0.105 | 0.105 | 0.105 | 0.105 | 0.105 | 0.105 | 0.105 |
| Ffww | 0.176 | 0.176 | 0.201 | 0.195 | 0.189 | 0.184 | 0.180 |
| Dia, mm | 57 | 57 | 57 | 57 | 57 | 57 | 57 |
| Afg | 13 | 13 | 13 | 13 | 13 | 13 | 13 |
| M/SME | 4.43 | 4.43 | 3.29 | 3.33 | 3.77 | 3.83 | 4.23 |
| ESPV | 1.0 | 1.0 | 1.1 | 1.1 | 1.2 | 1.2 | 1.3 |

All of the ESPVs were above 1.0.

COMPARATIVE EXAMPLE

Unacceptably sticky products were prepared by extruding B790 PURE-COTE® starch on a Wenger TX144 Twin Screw Extruder under the following conditions.

| Inputs | C-1A | C-1B | C-1C | C-1D | C-1E |
|---|---|---|---|---|---|
| SME, kW/ton | 86.9 | 76.4 | 103.6 | 140 | 150 |
| M, lbs/hr | 3800 | 4100 | 4100 | 3000 | 3000 |
| Mws, lbs/hr | 380 | 370 | 382 | 238 | 300 |
| $T_h$, deg F. | 269 | 269 | 269 | 293 | 305 |
| $T_l$, deg F. | 97 | 87 | 90 | 96 | 86 |
| Fws | 0.88 | 0.884 | 0.884 | 0.88 | 0.884 |
| Fww | 0.12 | 0.116 | 0.116 | 0.12 | 0.166 |
| Ffww | 0.200 | 0.189 | 0.191 | 0.185 | 0.196 |
| Dia, mm | 144 | 144 | 144 | 144 | 144 |
| Afg | 36 | 36 | 36 | 36 | 36 |
| M/SME | 43.73 | 53.66 | 39.58 | 21.43 | 20.00 |
| ESPV | 0.8 | 0.9 | 0.9 | 1.3 | 0.8 |

As seen, all but one of the ESPVs were below 1.0 in these examples. It is believed that, although the barrel temperature was allowed to vary in accordance with the invention, the moisture content in the barrel was too high to result in an acceptable product given the other conditions.

Thus, it is seen that the invention provides a satisfactory cold-water soluble starch. The starch may be prepared by extrusion in a conventional extruder.

While particular embodiments of the invention have been shown, it will be understood that the invention is not limited thereto since modifications may be made by those skilled in the art, particularly in light of the foregoing teachings. It is, therefore, contemplated by the appended claims to cover any such modifications as incorporate those features, which constitute the essential features of these improvements within the true spirit and scope of the invention. All references cited herein are hereby incorporated by reference.

What is claimed is:

1. An extruded starch product prepared by a process comprising:

providing a hydroxyalkyl starch, said starch being derivatized with a hydroxyalkyl substituent having from 2 to 6 carbon atoms; and extruding said starch in an extruder, said extruder having a barrel, a die, and at least one rotating shaft, said barrel having at least first and second zones, said first zone being upstream from said second zone, the temperature in said first zone being insufficient to gelatinize said starch and the temperature in said second zone being sufficient to gelatinize said starch, said starch being extruded in the presence of total moisture in said barrel no greater than about 25% by weight of said starch, said process including the step of controlling the rotational speed of said shaft to impart a specific mechanical energy to said starch sufficient to result in a soluble extruded starch product that is capable of extrusion through said die at said rotational speed, said starch being substantially completely soluble in water at 25° C. and being film-forming in aqueous solution.

2. A starch according to claim 1, said starch having a moisture content below about 15%.

3. A starch according to claim 1, said starch having a moisture content ranging from about 9% to about 12%.

4. A starch according to claim 1, said starch being a granular starch having a particle size distribution such that at least 90% by weight of the starch particles pass through a 180 micron screen prior to extrusion.

5. A starch according to claim 1, said starch being film-forming in aqueous solution and being gelatinized to a gelatinization level, said gelatinization level being at least 95%.

6. A starch product according to claim 1, said starch product being dried to a moisture content between about 9% and 12%.

7. A starch product according to claim 1, said starch product being a ground starch product.

* * * * *